(12) United States Patent
Bayer

(10) Patent No.: US 8,771,783 B2
(45) Date of Patent: Jul. 8, 2014

(54) IMPLANT AND METHOD FOR MANUFACTURING SAME

(75) Inventor: Ullrich Bayer, Admannshagen-Bargeshagen (DE)

(73) Assignee: Biotronik VI Patent AG, Baar (CH)

( * ) Notice: Subject to any disclaimer, the term of this patent is extended or adjusted under 35 U.S.C. 154(b) by 554 days.

(21) Appl. No.: 12/940,980

(22) Filed: Nov. 5, 2010

(65) Prior Publication Data

US 2011/0112628 A1 May 12, 2011

Related U.S. Application Data

(60) Provisional application No. 61/259,667, filed on Nov. 10, 2009.

(51) Int. Cl.
- *A61F 2/06* (2013.01)
- *B05D 3/04* (2006.01)
- *C23C 14/58* (2006.01)

(52) U.S. Cl.
USPC ......... 427/2.24; 427/2.25; 427/523; 427/532; 623/1.46

(58) Field of Classification Search
None
See application file for complete search history.

(56) References Cited

U.S. PATENT DOCUMENTS

2006/0229711 A1* 10/2006 Yan et al. ............... 623/1.38
2008/0243242 A1* 10/2008 Kappelt et al. ......... 623/1.46
2009/0118821 A1* 5/2009 Scheuermann et al. .... 623/1.49
2010/0087914 A1* 4/2010 Bayer et al. ............. 623/1.39
2010/0274352 A1* 10/2010 Kuehling et al. ........ 623/1.42

FOREIGN PATENT DOCUMENTS

EP 2087915 A2 8/2009
WO 2007082147 A2 7/2007

OTHER PUBLICATIONS

Cabanas et al. Calcium Phosphate coatings deposited by aerosol chemical vapor deposition. J. Materials Chemistry. vol. 13, 2003, pp. 1104-1107.*
Tian et al. Corrosion resistance improvement of magnesium alloy using nitrogen plasma ion implantation. Surface and Coatings Technology. 198 (2005) 454-458.*
Translation of CN 101496910 A retrieved Mar. 4, 2014.*
European Search Report for 10187880.9, Dec. 20, 2013.
Machine Translation of EP 2 087 915 A2, Aug. 12, 2009.
XP-002717485 & CN 101549170 A (Lifetech SCI Shenzhen Co Ltd) Oct. 7, 2009.

* cited by examiner

*Primary Examiner* — Cachet Sellman
(74) *Attorney, Agent, or Firm* — Biotech Beach Law Group, PC

(57) ABSTRACT

An implant, in particular an intraluminal endoprosthesis, is provided having an implant body containing biodegradable metallic material, preferably iron. To accelerate the degradation, at least a portion of the surface of the implant body has a first coating formed from a composition containing at least one element selected from the group including strontium and calcium. An inexpensive method for manufacturing such an implant is also described.

15 Claims, No Drawings

IMPLANT AND METHOD FOR MANUFACTURING SAME

CROSS REFERENCE TO RELATED APPLICATIONS

This invention claims benefit of priority to U.S. provisional patent application Ser. No. 61/259,667, filed on Nov. 10, 2009; the contents of which are herein incorporated by reference in their entirety.

FIELD OF INVENTION

The present invention relates to a method for manufacturing an implant, in particular an intraluminal endoprosthesis, having an implant body containing biodegradable metallic material, and a corresponding implant.

BACKGROUND OF THE INVENTION

A large variety of medical endoprostheses or implants for various applications are known from the prior art. Understood as implants within the meaning of the present invention are endovascular prostheses or other endoprostheses, for example stents, orthopedic implants such as attachment elements for bones, for example screws, plates, or pins, surgical suture material, intestinal clamps, vessel clips, prostheses for hard and soft tissue, and anchoring elements for electrodes, in particular for pacemakers or defibrillators.

Stents for the treatment of stenoses (vascular constrictions) are used particularly frequently as implants at the present time. Stents have a body in the form of an optionally perforated tubular or hollow cylindrical base lattice which is open at both longitudinal ends. The implant body of such an endoprosthesis is inserted into the vessel to be treated, and is used to support the vessel. Stents have become established in particular for the treatment of vascular diseases. Use of stents allows constricted regions in the blood vessels to be expanded, resulting in lumen gain. Although the optimal vessel cross section primarily necessary for successful treatment may be achieved by the use of stents or other implants, the permanent presence of such a foreign body initiates a cascade of microbiological processes which may lead to gradual overgrowth of the stent, and in the worst case may result in vascular occlusion. One approach to this problem is to fabricate the stent or other implants from a biodegradable material.

The term "biodegradation" refers to hydrolytic, enzymatic, and other metabolic degradation processes in the living organism which are primarily caused by the bodily fluids which come into contact with the biodegradable material of the implant, resulting in gradual disintegration of the structures of the implant containing the biodegradable material. As a result of this process, at a certain point in time the implant loses its mechanical integrity. The term "biocorrosion" is frequently used synonymously for "biodegradation." The term "bioabsorption" includes the subsequent absorption of the degradation products by the living organism.

Suitable materials for the body of biodegradable implants may include polymer or metals, for example. The body may be composed of several of these materials. The common feature of these materials is their biodegradability. Examples of suitable polymeric compounds include polymers selected from the group including cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, poly-ortho esters, polyethylene terephtalate (PET), polymalonic acid (PML), polyanhydrides, polyphosphazenes, polyamino acids, and the copolymer thereof, as well as hyaluronic acid. Depending on the desired characteristics, the polymer may be present in pure form, in derivatized form, in the form of blends, or as copolymer. Metallic biodegradable materials are primarily based on alloys of magnesium and iron. The present invention preferably relates to implants whose biodegradable material of the implant body contains, at least in part, a metal, preferably iron, in particular an iron-based alloy (referred to below as "iron alloy" for short).

In the implementation of biodegradable implants, the aim is to control the degradability corresponding to the intended treatment or use of the particular implant (coronary, intracranial, renal, etc.). For many therapeutic applications, for example, it is an important target corridor for the implant to lose its integrity over a period of four weeks to six months. In this regard "integrity," i.e., mechanical integrity, refers to the characteristic that the implant does not undergo hardly any mechanical losses compared to the nondegraded implant. This means that the implant is still mechanically stable enough to ensure that, for example, the collapse pressure drops only slightly, i.e., to a maximum of 80% of the nominal value. Thus, when integrity is present the implant is still able to fulfill its primary function of keeping the blood vessel open. Alternatively, integrity may be defined such that the implant is mechanically stable enough that in a load state in the blood vessel it undergoes minimal changes in its geometry, for example does not show appreciable collapse, i.e., under a load of at least 80% of the dilation diameter, or, in the case of a stent, has very little fracturing of supporting struts.

Implants containing an iron alloy, in particular iron-containing stents, are particularly economical and easy to manufacture. For the treatment of stenoses, for example, these implants do not lose their mechanical integrity or support effect until after a comparatively long time, i.e., after a residence time of approximately two years in the treated organism. This means that for implants containing iron, the collapse pressure decreases too slowly over time for the desired applications.

Various mechanisms for controlling the degradation of implants have been described in the prior art. These mechanisms are based, for example, on inorganic and organic protective layers or a combination thereof which resist the human corrosive environment and the corrosion processes occurring therein. Previously known approaches are characterized by the achievement of barrier layer effects which are based on spatially separating, with as few defects as possible, the corrosion medium from the metallic material. As a result, the degradation time is increased. This ensures degradation protection by use of protective layers of various compositions and by defined geometric distances (diffusion barriers) between the corrosion medium and the magnesium base material. Other approaches are based on modifying alloy components of the biodegradable material of the implant body in a targeted manner. However, the previously described approaches are usually not able to place the disintegration occurring due to the degradation process and the resulting strut fractures in the required time window. The result, in particular for implants having a body containing an iron alloy, is degradation of the implant which begins too late or which has excessive variability.

SUMMARY OF THE INVENTION

Consequently, an object of the present invention is to provide an inexpensive method for manufacturing an implant which brings about degradation of the implant in the desired time window, in particular for implants containing an iron-based alloy, in a rather short period of time. The aim is for the degradation to occur at a controllable point in time. Correspondingly, a further object of the invention is to provide such an implant.

The above object is achieved by use of an implant in which at least a portion of the surface of the implant body has a coating formed from a composition containing at least one element selected from the group including strontium and calcium.

DETAILED DESCRIPTION OF THE INVENTION

In the present invention the body of the implant includes at least a part of the implant, preferably the main part of the implant, which provides for mechanical integrity of the implant.

According to the invention, the composition for the coating may be composed either completely or partially of one or both of the referenced elements of the group, or may contain compounds having the referenced elements. The proportion of strontium in the coating is preferably approximately 10 to 20% by weight, and/or the proportion of calcium in the coating is approximately 5 to 10% by weight. These values are valid for layer thicknesses of up to 5 µm.

The implant according to the invention has the advantage that the degradation rate is significantly increased. As a result, the average residence time of the implant in the treated organism is shortened, and the metabolization of the material of the implant body is accelerated. In addition, for such an implant according to the invention, in particular when used as an orthopedic implant, the biocompatibility is increased since the strontium compounds released during the degradation favorably influence bone growth and thus improve the integration kinetics of the implant.

The increased degradation rate is achieved due to the fact that, on account of their great distance from iron in the electromotive series, strontium and calcium act as highly effective local elements and therefore corrode very quickly. As a result of this corrosion, after disintegration of the coating the surface of the implant body is so fissured that intensified surface corrosion and also an increasing degree of crevice corrosion occur. Thus, the integrated residence time of the implants according to the invention in the treated organism is reduced compared to uncoated implants.

In one preferred exemplary embodiment the body of the implant preferably contains a degradable metallic material, preferably predominantly iron, in particular greater than 80% by weight iron, particularly preferably at least 99% by weight iron, in particular in an alloy. Alternatively or additionally, manganese, zinc, and/or tungsten may be used as further metallic materials. Since they are inexpensive to manufacture, these implants are particularly favored for use in the treatment of diseases of the human or animal organism. In particular for implants containing iron, the coating according to the invention results in a shortened degradation period. In this manner a gap is closed between the degradable and non-degradable alloys for implants.

With regard to cost and in relation to the desired degradation period, a practical layer thickness of the coating having a composition containing at least one element from the group including strontium and calcium (referred to below as "Sr/Ca coating" for short) results when the thickness of the Sr/Ca coating is approximately 0.5 µm to approximately 10 µm, preferably approximately 1 µm to approximately 5 µm.

In order to achieve a localized variation of the degradation of the implant body as well as a greater depth of penetration of strontium and calcium into the implant body, in one particularly preferred embodiment the implant contains implanted nitrogen in the coating and in the implant body. The implantation is achieved by bombardment of the Sr/Ca-coated implant with nitrogen ions. The integrated nitrogen content from the surface of the Sr/Ca coating down to a depth of 5 µm is between 0.1% and 1.5% by weight. The integrated nitrogen content is calculated by taking the ratio of the total mass of nitrogen contained in the volume extending from the surface down to the referenced depth to the mass of the total substance mixture having the same volume. The nitrogen concentration is detectable down to a depth of 200 nm using XPS, and to greater depths using EDX.

As the result of this subsequently performed implantation of nitrogen ions into the implant, Sr and Ca ions are thermally excited and are caused to diffuse into the lattice of the implant body material, preferably into the iron lattice. This results in an element gradient which extends over the near-surface regions of the implant body and the Sr/Ca coating, regardless of the particular implantation carried out and the parameters thereof. For a very high implantation rate there is a comparatively high content of strontium and/or calcium ions in the implant body; at a high implantation rate the Sr or Ca ions also penetrate comparatively deeply into the implant body. As a whole, the content of strontium and/or calcium ions outwardly increases through the affected regions of the implant body and through the coating to the exterior. However, the change in the content over the stated region is dependent on the implantation rate.

In addition, it is particularly advantageous to also provide on the Sr/Ca coating a second coating containing an acid-degradable polymer, for example a polylactide, a polyglycoside, or a copolymer of same, particularly preferably PLLA or PLGA, or a blend of the referenced polymers. This polymer may also contain a pharmaceutically active substance. The lowering of the pH in the region of the implant surface caused by degradation of the polymer represents an additional acceleration factor for the corrosion, in particular for an implant containing an iron alloy.

The term "pharmaceutically active substance" (or therapeutically active substance, active ingredient) within the meaning of the invention refers to a plant, animal, or synthetic active substance (medicament) or a hormone which in appropriate dosages is used as a therapeutic agent for influencing states or functions of the body, as a substitute for active substances such as insulin which are naturally produced by the human or animal body, and for eliminating or rendering harmless pathogenic agents, tumors, cancer cells, or substances foreign to the body. The release of the substance into the environment of the implant has a positive effect on the healing process, or counteracts pathological changes in the tissue resulting from surgical procedures, or in the field of oncology is used to render malignant cells harmless.

These types of pharmaceutically active substances have an anti-inflammatory and/or antiproliferative and/or spasmolytic effect, for example, by means of which restenosis, inflammation, or (vascular) spasms, for example, may be avoided. Such substances may be composed, for example, of one or more substances from the active substance group of calcium channel blockers, lipid regulators (fibrates, for example), immunosuppressants, calcineurin inhibitors (tacrolimus, for example), antiphlogistic agents (cortisone or dichlofenac, for example), anti-inflammatory agents (imidazole, for example), antiallergic agents, oligonucleotides (dODN, for example), estrogens (genistein, for example), endothelium-forming agents (fibrin, for example), steroids, proteins, hormones, insulins, cytostatic agents, peptides, vasodilators (sartane, for example), and substances with antiproliferative activity, taxole or taxane, in the present case preferably paclitaxel or sirolimus.

The above object is achieved by use of a method including the steps of: (a) providing the implant body; and (b) coating the implant body with a composition containing at least one element selected from the group including strontium and calcium. An increased degradation rate of implants as described in greater detail above is achieved in a very economical manner by use of such a method.

In one preferred embodiment the coating is carried out by deposition from the gas phase. For this purpose the elements strontium and/or calcium are thermally evaporated in a treatment chamber, optionally with or without vacuum assistance. The medical implants placed in the treatment chamber are thus coated on all sides or, if appropriate masking is applied, are coated partially with the evaporated elements. The application by deposition from the gas phase has the advantage that even components having geometrically complicated shapes, such as coronary stents, may be uniformly coated on the cut edges and in undercuts.

In one preferred exemplary embodiment nitrogen ions are implanted in the implant body provided with the Sr/Ca coating. This subsequent implantation of nitrogen ions into the Sr/Ca coating, as described above, results in a gradient of strontium and/or calcium ions over the near-surface regions of the implant body and the Sr/Ca coating, depending on the particular implantation conditions present, which among other things results in increased adhesion of the Sr/Ca coating to the implant body. Localized changes in the concentration gradient of strontium and/or calcium may also be achieved by means of the beam guidance during ion implantation. This is advantageous, for example, in narrow radii between struts of a stent or in boreholes of bone plates. A locally differentiated implantation rate also results in differences in the depth of penetration of the strontium and/or calcium ions into the implant body. Accordingly, the beam guidance for the ion implantation may be controlled in such a way that zones of the implants which have only a minor supporting function in subsequent use are omitted from the ion implantation. When implants treated in this way are used under physiological conditions, they degrade according to the invention, with localized differences in an intended manner. The degradation rate may thus also be locally adjusted in a targeted manner. The degradation rate is highest at the locations having the highest concentration of implanted nitrogen ions, i.e., where the depth of penetration of the strontium and/or calcium ions is greatest.

In a further preferred exemplary embodiment the coated implant body is packaged under shielding gas to avoid immediate oxidation of the surface of the coated implant.

In a further exemplary embodiment, subsequent to the application of this coating or optionally following the nitrogen ion implantation a second coating may be applied to the Sr/Ca coating which contains acid-degradable polymer, for example a polylactide, a polyglycoside, or a copolymer of same, particularly preferably PLLA or PLGA, or a blend of the referenced polymers. This polymer may also contain a pharmaceutically active substance. Such a second coating has the advantages stated above. This type of second coating is preferably provided by spraying or by dipping into a diluted polymer solution. In the latter option the solvent is subsequently thermally stripped.

The object stated above is further achieved by use of an implant which may be obtained by a method according to the invention described above. Such an implant has the advantages stated above in conjunction with the manufacturing method according to the invention.

The method according to the invention and the implant according to the invention are further explained in the examples below. All described features constitute subject matter of the invention, regardless of their summary in the claims or back references.

EXAMPLE 1

Finished, processed stent bodies made of pure iron (99.5%) are placed in the degreased state in a vacuum chamber. A target composed of an alkaline earth metal, for example strontium, is present at the base of this chamber. After application of a vacuum of approximately $1 \times 10^{-4}$ Pa the Sr target is heated above the melting point of 777° C. The resulting gaseous strontium then deposits in solid form on all sides of the implant body. There is no thermal stress on the substrate. After a vaporization period of approximately 2 hours a layer thickness of approximately 2 µm is attained. The treatment chamber is then flushed with argon and the coated stent bodies are packaged under argon, using an air lock. This measure is used to prevent premature oxide formation on the strontium layer, which has a high affinity for oxygen.

In an additional coating facility flooded with argon the strontium-coated stent body is mounted on a sample holder in such a way that the ion beam is able to move over the entire outer surface. Implantation of nitrogen ions is then performed at a power level of 40 keV and a dose of approximately $4 \times 10^{17}$ cm$^{-2}$. Alloy formation between Fe and Sr does not occur. However, a portion of the implanted nitrogen is dissolved in the Fe matrix of the stent body, and an additional portion forms Fe nitrides with the iron present in the stent body, causing surface hardening.

Due to the unavoidable shadowing effects of the complicated stent geometries, the interior of the irradiated stent body, for example, receives a dose of only approximately $1 \times 10^{17}$ cm$^{-2}$. The force toward diffusion of strontium into the interior of the implant body which is thermodynamically initiated by the nitrogen implantation causes the thickness of the Sr-containing top layer to increase from approximately 2 µm to approximately 3 µm. The irradiation by nitrogen ions creates internal friction at the surface of the stent which causes heating of the surface on a microscopic scale. This facilitates the diffusion of the Sr ions. At a depth greater than 3 µm, Sr is no longer detectable using spatially resolved EDX.

After removal from the treatment chamber the stents are exposed to physiological conditions of the body (aqueous electrolyte). The Sr layer of the stent interior, which is only slightly bonded by nitrogen ions, degrades more slowly than the outer surface of the stent which has been irradiated with a higher dose.

The aqueous electrolyte containing chloride ions quickly converts the strontium in the coating on the inner surface to the very water-soluble strontium hydroxide. However, the corrosive attack drops afterward due to a certain degree of micropassivation of the iron surface as a result of the basic environment which is created.

The outer surface of the stent behaves differently. In this case the strontium, which is compressed in the iron matrix of the implant body by nitrogen, is able to effectively develop its activity as a galvanic element. Intensified pitting and crevice corrosion result. These mechanisms appear in heightened form even when the corrosion has already reached deeper, strontium-free zones. The surface corrosion mechanism then has an increased effect as a result of the high fissure rate. At the outer surface of the stent the repassivation effect is far outweighed by the metal disintegration. The stent treated in this manner in simulated body fluid (SBF) at 37° C. degrades 1.5 times more quickly than an uncoated iron stent of identical composition.

EXAMPLE 2

Example 2 was carried out analogously to Example 1, likewise using a stent body made of pure iron (99.5%). In this case calcium with a purity level of 95% was used as the target. After application of a vacuum of approximately $1\times10^{-4}$ Pa the Ca target was heated above the melting point of 839° C. The further procedure and the other parameters correspond to Example 1.

EXAMPLE 3

Example 3 was carried out analogously to Example 1. However, in this example a target composed of a Sr alloy containing approximately 18.25% Al was used. This eutectic alloy has a melting point of 590° C. Consequently, the evaporation temperature may be decreased. Alternatively, when a higher temperature is set the deposition rate may be increased, thereby shortening the treatment time. The other parameters and the procedure correspond to Example 1.

EXAMPLE 4

Starting from Example 1 or 2, the process of implantation of nitrogen ions was dispensed with. Thus, additional nitrogen ions were not implanted. Consequently, corrosion rates which are not locally differentiated may also be set. The implant then acts primarily as a Sr or Ca reservoir with the described advantages for osteosynthesis. The degradation rate was 1.0 to 1.5 times as high when used as an orthopedic implant. The specific degradation behavior depends on the implant geometry. Filigreed implants such as bone screws or radius plates for children degrade more quickly (factor of 1.5) than, for example, bone plates for humeral fractures in adults (factor of 1.2) due to the larger surface/volume ratio.

EXAMPLE 5

Example 5 was carried out analogously to one of Examples 1 through 4, and after application of the Sr/Ca coating, or after the nitrogen implantation if applicable, an acid-degradable polymer layer, for example PLLA L 210 or PLGA, was provided on the Sr/Ca coating as a topcoat. A pharmaceutically active substance may optionally be incorporated into the polymer layer. The topcoat was applied in a treatment chamber at standard pressure and room temperature, using a spray process. This was followed by an annealing process: for PLGA, over a period of 13 h at 40° C.; for PLLA L 210, over a period of 13 h at 80° C.

The advantage of the topcoat is that at the start of degradation an acid degradation product is initially produced in vivo. This acid degradation product interacts with the basically reacting Sr and Ca layers. In total, a rapid neutralization of the implant environment occurs. In this manner an inflammatory reaction of the surrounding tissue cells is suppressed, since the concentration of hydrogen ions in the environment does not significantly deviate from pH 7.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method for manufacturing an implant, in particular an intraluminal endoprosthesis, having an implant body containing biodegradable iron, comprising the following steps:
   a) providing the implant body;
   b) coating the implant body with a composition containing at least one element selected from the group consisting of strontium and calcium, whereby the coating in step b) is carried out by deposition from a gas phase; and
   c) implanting nitrogen ions in the coated implant body.

2. The method according to claim 1, further comprising the step of applying a coating containing an acid-degradable polymer to the coated implant body, wherein the acid degradable polymer contains a pharmaceutically active substance is selected from the group consisting of a calcium channel blocker, a lipid regulator, an immunosuppressant, a calcineurin inhibitor, an anti-inflammatory agent, an endothelium-forming agent, a cytostatic agent, and a vasodilator.

3. The method according to claim 1, further comprising the step of applying a coating containing an acid-degradable polymer to the coated implant body, wherein the acid degradable polymer contains a pharmaceutically active substance comprising paclitaxel or sirolimus.

4. A method for manufacturing an implant, in particular an intraluminal endoprosthesis, having an implant body containing biodegradable iron, comprising the following steps:
   a) providing the implant body;
   b) coating the implant body with a composition containing at least one element selected from the group consisting of strontium and calcium, whereby the coating in step b) is carried out by deposition from a gas phase; and
   c) applying a coating containing an acid-degradable polymer to the coated implant body.

5. The method according to claim 4, wherein the polymer contains a pharmaceutically active substance.

6. The method according to claim 5, wherein the pharmaceutically active substance is selected from the group consisting of a calcium channel blocker, a lipid regulator, an immunosuppressant, a calcineurin inhibitor, an anti-inflammatory agent, an endothelium-forming agent, a cytostatic agent, and a vasodilator.

7. The method according to claim 5, wherein the pharmaceutically active substance comprises paclitaxel or sirolimus.

8. The method according to claim 5, wherein the pharmaceutically active substance is for the treatment of a condition selected from the group consisting of restenosis, inflammation, and vascular spasm.

9. A method for manufacturing an implant, in particular an intraluminal endoprosthesis, having an implant body containing biodegradable iron, comprising the following steps:
   a) providing the implant body; and
   b) coating the implant body with a composition containing strontium, whereby the coating in step b) is carried out by deposition from a gas phase.

10. The method of claim 9, further comprising treating the coated implant to insert strontium ions into a lattice of the implant body.

11. The method according to claim 9, further comprising implanting nitrogen ions in the coated implant body.

12. The method according to claim 9, further comprising applying a coating containing an acid-degradable polymer to the coated implant body, wherein the acid degradable polymer contains a pharmaceutically active substance selected from the group consisting of a calcium channel blocker, a lipid regulator, an immunosuppressant, a calcineurin inhibitor, an anti-inflammatory agent, an endothelium-forming agent, a cytostatic agent, and a vasodilator.

13. The method according to claim 9, further comprising applying a coating containing an acid-degradable polymer to the coated implant body, wherein the acid degradable polymer contains a pharmaceutically active substance comprising paclitaxel or sirolimus.

14. A method for manufacturing an implant, in particular an intraluminal endoprosthesis, having an implant body containing biodegradable iron, comprising the following steps:
   a) providing the implant body;
   b) coating the implant body with a composition containing at least one element selected from the group consisting of strontium and calcium, whereby the coating in step b) is carried out by deposition from a gas phase; and
   c) treating the coated implant to insert strontium ions or calcium ions into a lattice of the implant body.

15. The method according to claim 14, further comprising applying a coating containing an acid-degradable polymer to the coated implant body, wherein the acid degradable polymer contains a pharmaceutically active substance comprising paclitaxel or sirolimus.

\* \* \* \* \*